(12) United States Patent
Goldmeier

(10) Patent No.: US 10,743,796 B2
(45) Date of Patent: Aug. 18, 2020

(54) WHEELCHAIR FOOT SENSOR ALARM

(71) Applicant: Steven Goldmeier, Plainview, NY (US)

(72) Inventor: Steven Goldmeier, Plainview, NY (US)

(*) Notice: Subject to any disclaimer, the term of this patent is extended or adjusted under 35 U.S.C. 154(b) by 0 days.

(21) Appl. No.: 16/676,191

(22) Filed: Nov. 6, 2019

(65) Prior Publication Data

US 2020/0138338 A1    May 7, 2020

Related U.S. Application Data

(60) Provisional application No. 62/757,059, filed on Nov. 7, 2018.

(51) Int. Cl.
*A61B 5/11* (2006.01)
*A61B 5/00* (2006.01)

(52) U.S. Cl.
CPC .......... *A61B 5/1115* (2013.01); *A61B 5/6894* (2013.01); *A61B 5/742* (2013.01); *A61B 5/7405* (2013.01); *A61B 5/746* (2013.01)

(58) Field of Classification Search
CPC ... A61B 5/1115; A61B 5/6894; A61B 5/7405; A61B 5/742; A61B 5/746; G08B 21/00; G08B 21/02
USPC ........................................................ 340/439
See application file for complete search history.

(56) References Cited

U.S. PATENT DOCUMENTS

| | | | | |
|---|---|---|---|---|
| 5,844,488 A | * | 12/1998 | Musick | G08B 21/22 340/573.4 |
| 6,163,249 A | * | 12/2000 | Betcher, III | A45B 9/00 135/65 |
| 9,757,054 B2 | * | 9/2017 | Hyde | A61B 5/6894 |
| 2001/0001237 A1 | * | 5/2001 | Stroda | A61B 5/1117 340/573.4 |
| 2006/0181374 A1 | * | 8/2006 | Lee | H01H 36/0046 335/78 |
| 2010/0045454 A1 | * | 2/2010 | Knight | G08B 21/0453 340/521 |
| 2015/0045630 A1 | * | 2/2015 | Poliakine-Baruchi | A61B 5/7475 600/301 |
| 2015/0216449 A1 | * | 8/2015 | Fleischer | A61B 5/742 340/626 |
| 2015/0245961 A1 | * | 9/2015 | Pettigrew | G05B 19/0426 701/33.1 |
| 2020/0060905 A1 | * | 2/2020 | Bogie | A61G 5/00 |

* cited by examiner

*Primary Examiner* — Eric Blount
(74) *Attorney, Agent, or Firm* — Alfred M. Walker

(57) ABSTRACT

A foot sensor alarm for wheelchairs, detects if a wheelchair occupant's foot has fallen off of a wheelchair footrest. The sensor and alarm make a wheelchair occupant or care giver aware that a foot has fallen off of one or more of the footrests. Sensors may include contact closure sensors, with snap-action switches or magnetically actuated reed switches can be used. Battery-operated window alarms with piezo-electric sound emitters send out vibratory or audio sounds as alarms. An occupancy sensor seat pad is used to power up the alarm system. A flashing light emitting diode can be wired in parallel with each sound emitter to provide a visual alarm as well.

21 Claims, 6 Drawing Sheets

WHEELCHAIR FOOT SENSOR ALARM

RELATED APPLICATIONS

This application is based upon U.S. provisional patent application No. 62/757,059 filed Nov. 7, 2018. Applicant claims priority under 35 USC section 119 (e) and claims priority therefrom. The '059 application is incorporated by reference herein in its entirety.

FIELD OF THE INVENTION

The present invention relates to sensors and a foot sensor alarm for wheelchairs, to detect if a wheelchair occupant is aware that an occupant's foot has fallen off of a wheelchair footrest.

BACKGROUND OF THE INVENTION

Often a person using a wheelchair has loss of sensation in one or both legs. He or she would have no location awareness of one or both feet on the footrest or rests of the wheelchair. If a person's foot were to fall off a footrest, the foot could drag on the ground and get severely injured. This is especially problematic for independent wheelchair occupants of powered wheelchairs.

The present invention uses sensors and alarms to make a wheelchair occupant or care giver aware that a foot has fallen off the footrest.

OBJECTS OF THE INVENTION

It is therefore an object of the present invention to provide a foot sensor alarm for wheelchairs, to detect if a wheelchair occupant's foot has fallen off of a wheelchair footrest.

It is also an object of the present invention to provide vibratory, sound or visual alarms to notify a wheelchair occupant or care giver that one or both feet of the wheelchair occupant have fallen off of the respective footrests of the wheelchair.

Other objects which become apparent from the following description of the present invention.

SUMMARY OF THE INVENTION

The sensors and alarms of this invention can be factory installed or retrofitted to a wheelchair. They have their own separate power supply and do not borrow power or otherwise interfere with the controls of a powered wheelchair; the invention can be added to a manual wheelchair as well.

Although other implementation choices are possible, sensors of the contact closure type are used in the drawing examples. Either miniature snap-action switches or magnetically actuated reed switches can be readily used; the latter have been selected due to ease of mounting and protection from the elements. No sophisticated electronics are used. Other components used are widely available for large-market applications. Reed switches and actuating magnets are used in inexpensive battery-operated window alarms with piezoelectric sound emitters; both of these components are used in this invention.

Two separate foot sensor pedals are used atop the exact location for each foot on the wheelchair footrest (or separate rests respectively). These pedals are hinged at one end and lifted slightly at the distal ends from the footrests underneath by the action of spring elements. The distance is of the order of ⅛". An actuating magnet is attached under the front end of each pedal. A reed switch is strategically attached to the footrest frame so that it is not actuated by the magnet when the pedal is up, but detects a pedal in the down position flat with the footrest when a foot is resting atop.

An occupancy sensor seat pad is used to power up the alarm system. Two small plastic housings each contain a piezo sound emitter, one as a left foot alarm and one as a right foot alarm. These should be mounted on the left and right wheelchair arms respectively. One plastic housing is larger than the other since it also houses the battery pack. A flashing light emitting diode can be wired in parallel with each sound emitter to provide a visual alarm as well.

For example, in a preferred embodiment, the alarm system for a wheelchair, where the wheelchair includes a seat, arm rests, a back rest, and one or more footrests adapted to each support a foot of a user; includes a sensor pedal mounted on the footrest. The sensor pedal extends along one edge thereof from a flexible joint, such as a spring hinge, which is attached to each footrest, so that the flexible joint or spring hinge biases biasing a distal end of each sensor pedal away from each footrest. An actuator, such as an actuating magnet, is attached by bonding or otherwise, to an underside of each distal end of each sensor pedal.

A normally closed sensor switch is mounted on each footrest opposite the actuator or magnet whereas there is a gap between actuator or magnet and the sensor switch when each respective footrest is unoccupied. The sensor switch is part of an electric circuit which issues an alarm when at least one footrest becomes unoccupied when the wheelchair is being occupied. The gap is closed when each respective footrest is being occupied, and each respective actuator or magnet is in close proximity to each respective sensor switch, to maintain each sensor switch in an open position wherein the electric circuit is open and inactive.

The respective gap, upon being opened when the respective footrest becomes unoccupied, causes the respective sensor switch to close the electric circuit, resulting in one or more audible and/or visual alarms being issued.

Furthermore, an on-off switch is mounted in the seat for turning on the electric circuit when the wheelchair is occupied.

BRIEF DESCRIPTION OF THE DRAWINGS

The present invention can best be understood in connection with the accompanying drawings. It is noted that the invention is not limited to the precise embodiments shown in the following drawings, in which.

DETAILED DESCRIPTION OF THE DRAWINGS

For illustrative purposes only, a preferred mode for carrying out the invention is described herein.

Figure 1:
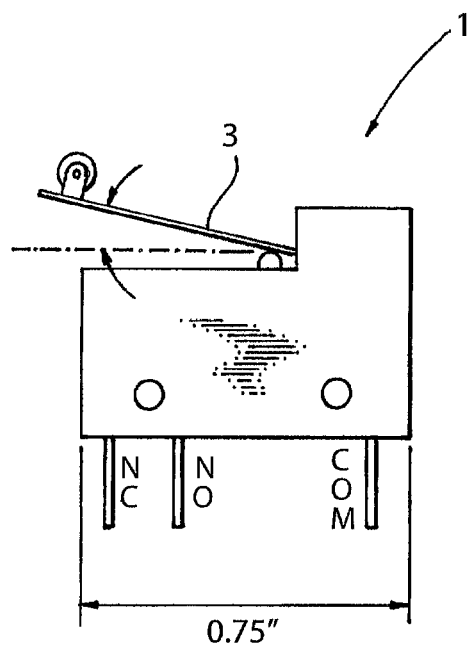
FIG. 1 is a front elevation of a typical snap-action switch.
Figure 2:
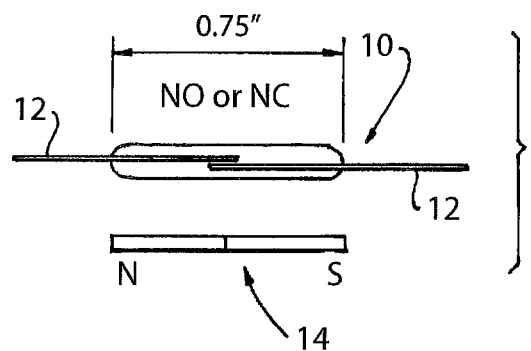
FIG. 2 is a side elevation of a reed switch with activating magnet.
Figure 3:
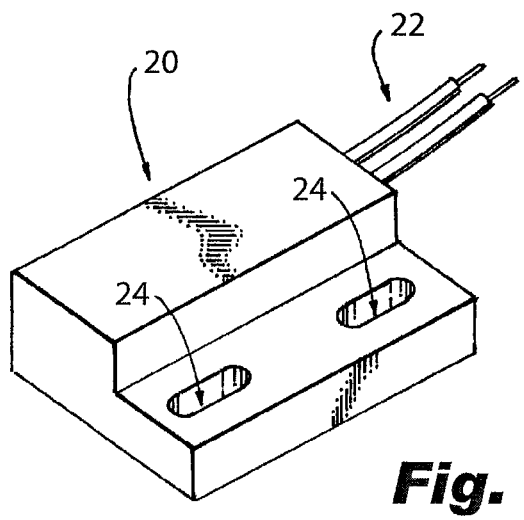
FIG. 3 is a perspective view of a reed switch in a plastic case with mounting features.

FIG. 1 shows a switch, such as a miniature snap-action switch 1. While other switches may be employed, a miniature snap action switch 1 is a very inexpensive, reliable, and small device. It is noted that it has three terminals at the bottom labeled NC, NO, and COM. Switch 1 is a single-pole double-throw (SPDT) type. Actuating lever 3 can detect motions less than 0.1" reliably. FIG. 2 shows a magnetic reed switch 10 and an actuating magnet 14. It can be obtained as a normally open (NO) or normally closed (NC) type. Reed switch 10 is a basic element that has a tubular glass housing with hermetically sealed contacts. It can be less than 1/10" in diameter. FIG. 3 shows an element such as switch 10 encased in a robust housing 20 with mounting features such as holes 24. Flexible wires 22 can be sealed from water or debris damage.

Figure 4:
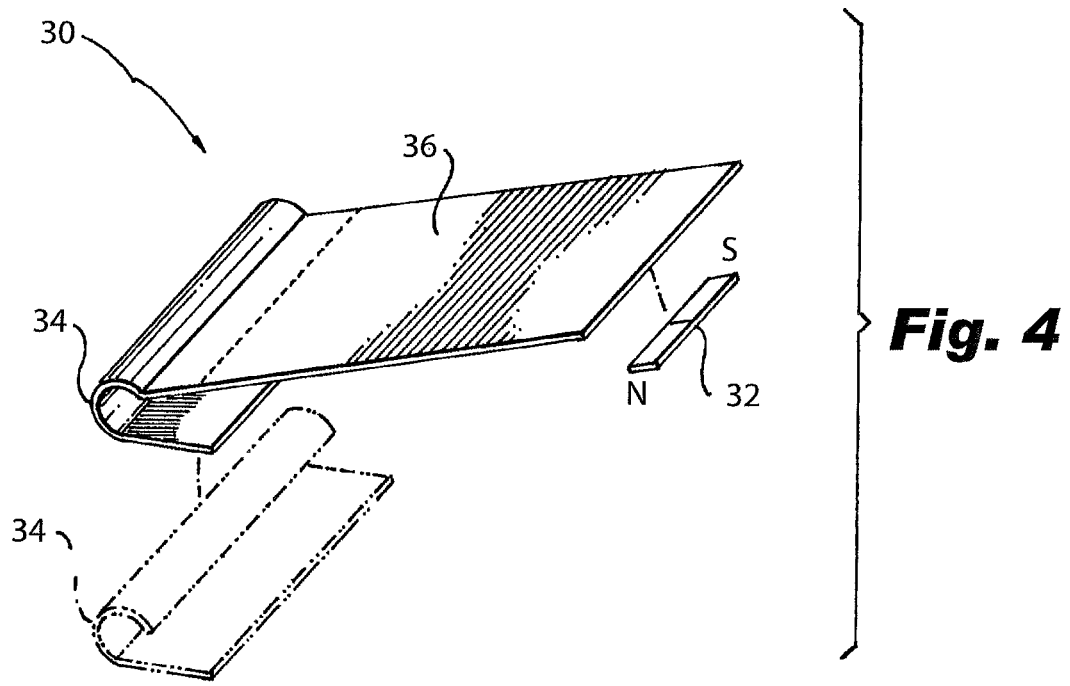
FIG. 4 is an exploded view of a foot pedal used for sensing presence of a foot.
Figure 5A:
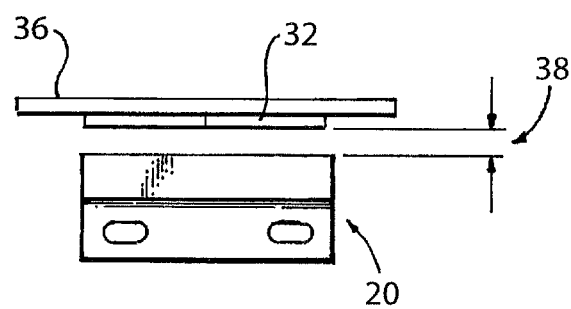
FIG. 5A is a front detail of a pedal in the up position (an alarm situation)
Figure 5B:
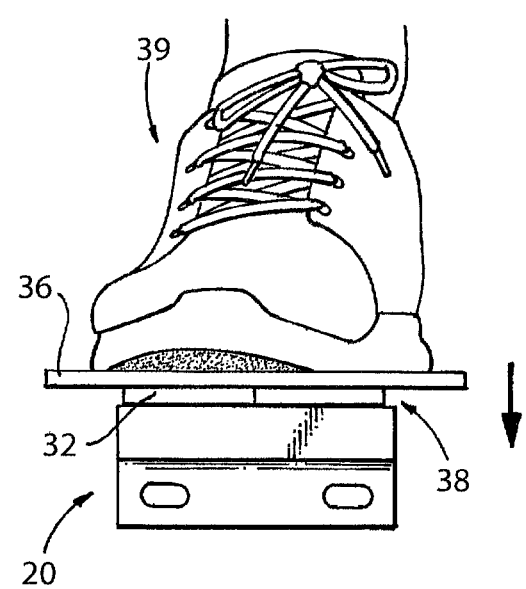
FIG. 5B is a front detail of a pedal in the down position (detecting a foot)

FIG. 4 shows a method of fabricating a sensor pedal 30. A rigid flat foot surface 36 is used as the base. One material that can be used for this part is 3 mm thick closed cell PVC foam sheet, which is light weight, rigid and resistant to exposure (it is typically used for signage and is sold under the trade name of SINTRA®). The flexible joint, such as a spring hinge 34, is adhesively bonded or otherwise attached to base 36 and to wheelchair footrest; preferably a formed sheet of spring grade stainless steel is used. An actuator, such as an actuating magnet 32, is bonded at the front of base 36. The views of FIGS. 5A and 5B show that gap 38 between magnet 32 and sensor 20 disappears when a foot 39 is placed on foot pedal 30-foot surface 36.

Figure 6:
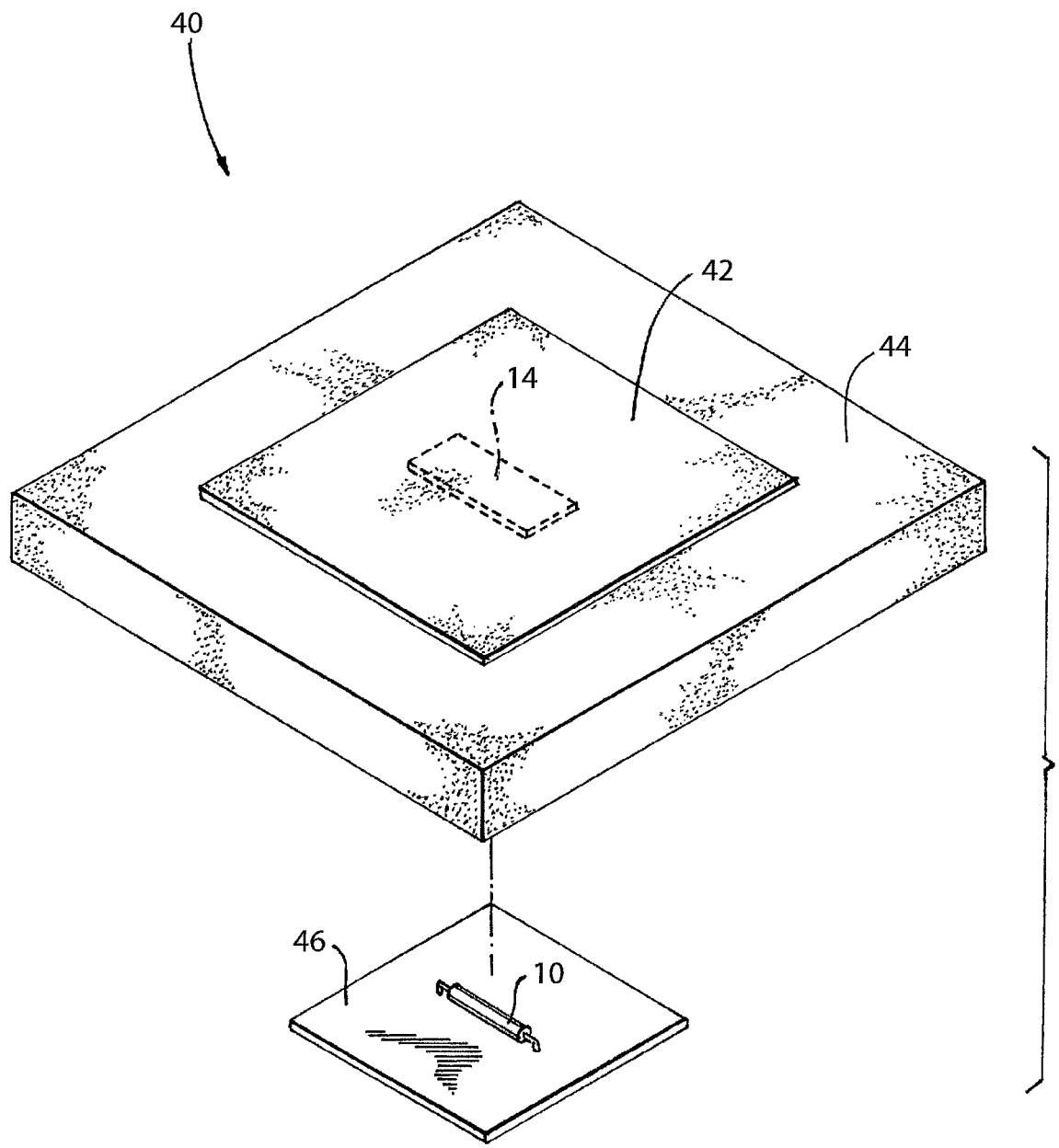
FIG. 6 is an exploded view of a chair pad for occupancy detection.

FIG. 6 shows a seat occupancy detection pad 40, preferably as assembled from a small piece of printed circuit board 46 such as FR-4 with a mounted reed switch element 10 at the bottom. It is noted that reed switch 10 is preferably ruggedized by encasing it in a protective covering, such as, for example, a small piece of brass or other metallic or synthetic plastic tubing. It is bonded to a resilient pad, such as a foam rubber pad 44 with flexible rubber or other material 42 covering the actuator, such an actuating magnet 14. Other coverings for occupant comfort (not shown) are added. Occupancy detector pad 40 is actuated by the presence of a weight atop the pad, compressing foam pad 44, bringing magnet 14 closer to reed switch 10.

Figure 7:
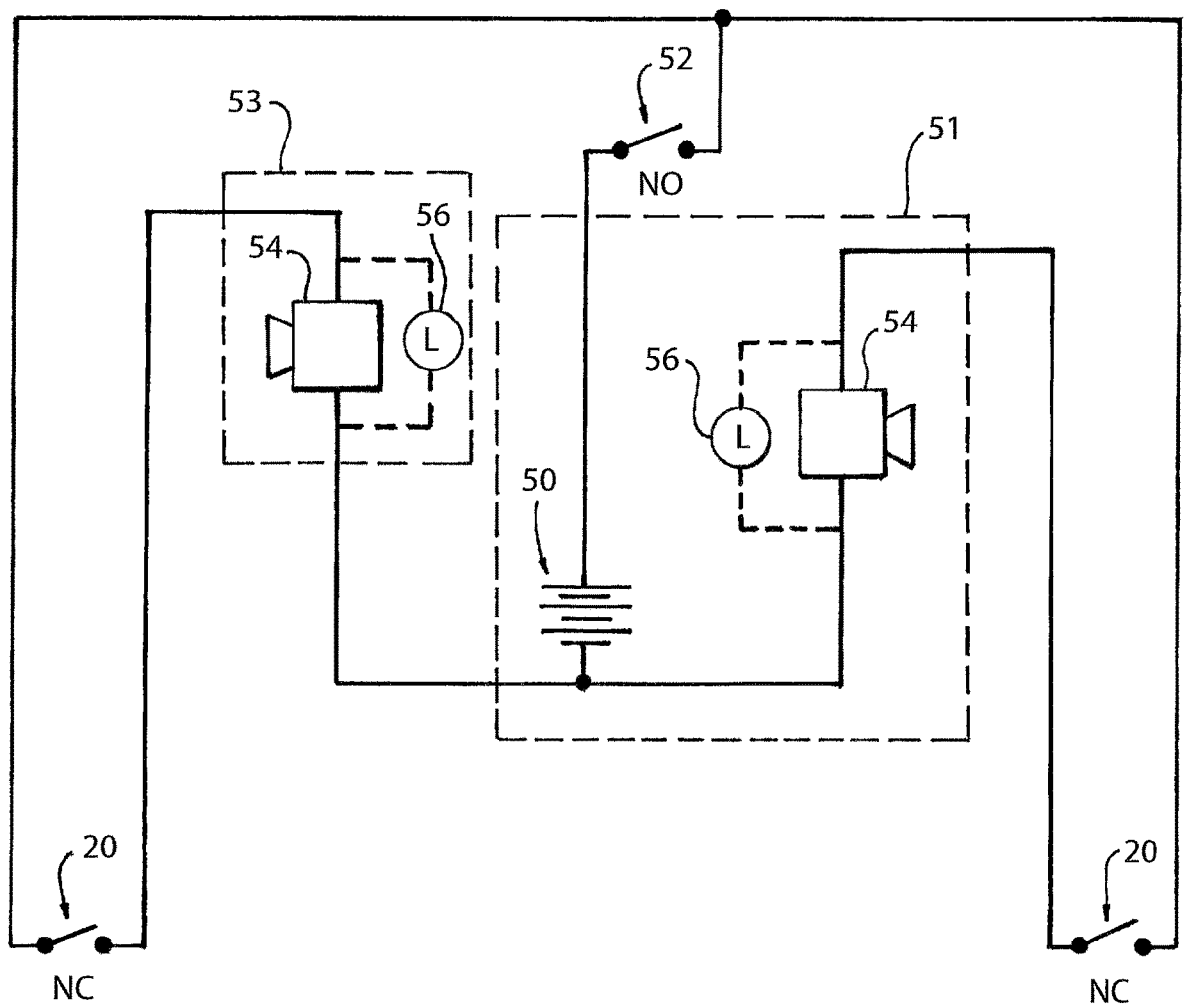
FIG. 7 is a schematic diagram showing the connections between sensors and alarms.

FIG. 7 is a schematic wiring diagram. While other power sources may be used, battery 50 is shown with three AA alkaline cells in series yielding a nominal 4.5 volts. While a single audible alarm may be provided for either foot being off of a respective footrest, preferably, two piezo sound emitters 54 are used, one for the left foot and one for the right foot respectively. Two normally closed reed switches adjacent to pedals 30 detect foot position. While any relevant sensor switch may be used, preferably occupancy sensor switch 52 can be fabricated like switch 40 in FIG. 6 using a normally open reed switch 10, or it can be any commercially available type that is normally open and can switch a minimal amperage, preferably at least 1/10 ampere. Housing 51 contains battery 50, sound emitter 54 and an optional flashing LED 56. Housing 53 just contains a sound emitter 54 and an optional flashing LED 56. The operation is quite straight forward. If there is no occupant, switch 52 is off and all operation is interrupted. If switch 52 senses a person, and the right foot pedal 30 has no foot on it, the right sound emitter 54 starts blaring. If the left foot pedal 30 has no foot on it, the left sound emitter 54 starts blaring. Right side and left side operate independently. If both feet are on their respective pedals, no alarms sound. By not having an on/off switch besides the occupancy switch, there is no chance of a wheelchair occupant or care giver forgetting to turn it ON. As there will be short instances of not both feet on the pedals while the seat is occupied (i.e. while getting IN or OUT of the seat) one or both of the alarms should sound. That would be a good check of the alarm system and battery condition. It is noted that this wiring diagram also permits the substitution of other switches, such as, for example, miniature snap action switches 1 for reed switches using the appropriate switch terminals, NC or NO.

Figure 8:
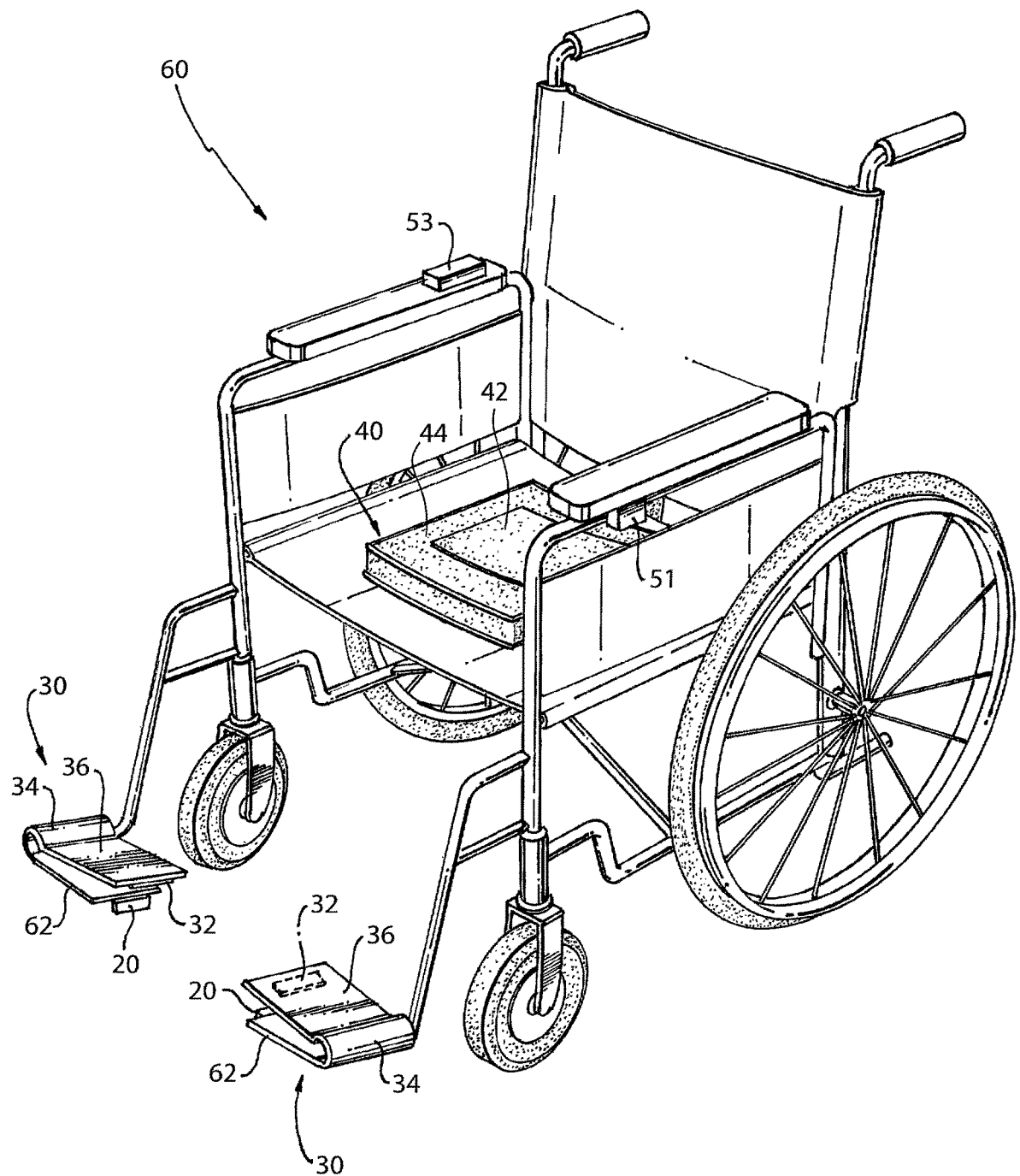
FIG. 8 is a perspective view of a manual wheelchair with the alarm system of this invention installed; and, FIG. 9 is a perspective view of a powered wheelchair with the alarm system of this invention installed.

FIG. 8 shows the elements of this invention installed on a manual wheelchair 60. While any safe configuration can be employed, it is noted that pedals 30 are preferably hinged at the side since separate footrests 62 are used. It is further noted that housing 51 can be preferably attached under the arm rest. Housing 53 is shown attached on top of the other arm rest. Both housings can be moved to the upper back for better sound location.

Figure 9:
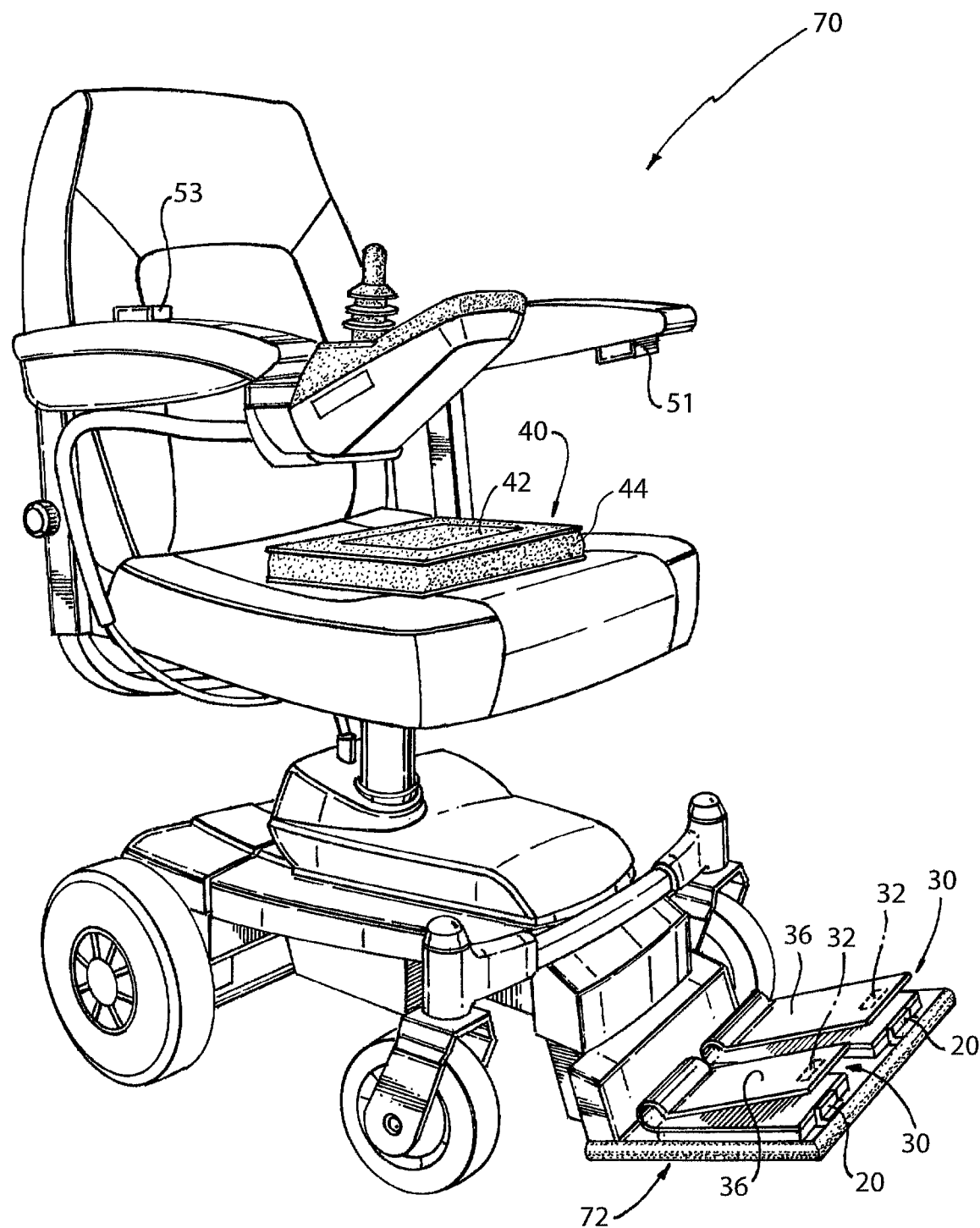

FIG. 9 shows an installation on a powered chair 70. It is noted here that wheelchair 70 has a single footrest 72 for both feet. Separate pedals 30 (here hinged at the back) are still required to indicate which foot is not on the footrest.

It is further noted that what is illustrated herein for a manual wheelchair can also be used with a powered wheelchair, and vice versa. For example, either a powered wheelchair or a manual wheelchair can have a separate pair of footrests, or a single footrest for both feet. However, separate pedals and sensors are still required on wheelchairs with a single side to side extending footrest.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention.

I claim:

1. An alarm system for a wheelchair comprising:
    said wheelchair comprising a seat, arm rests, a back rest, and a footrest adapted to support a foot of a user;
    a sensor pedal mounted on said footrest, said sensor pedal extending along one edge thereof from a spring hinge attached to said footrest, said spring hinge biasing a distal end of said sensor pedal away from said footrest;
    an actuating magnet bonded to an underside of said distal end of said sensor pedal;
    a normally closed sensor switch mounted on said footrest opposite said magnet whereas there is a gap between said magnet and said sensor switch when said footrest is unoccupied;
    said sensor switch being part of an electric circuit which issues an alarm when said footrest becomes unoccupied when said wheelchair is being occupied;
    said gap being closed when said footrest is being occupied, said magnet being in close proximity to said sensor switch to maintain said sensor switch in an open position wherein said electric circuit is open and inactive, said gap upon being opened when said footrest becomes unoccupied causing said sensor switch to close said electric circuit resulting in an alarm being issued; and an on-off switch mounted in said seat for turning on said electric circuit when said wheelchair is occupied.

2. The alarm system of claim 1 in which said wheelchair has two footrests, each footrest having a sensor pedal and a sensor connected in parallel to said electric circuit for creating an alarm in the event either footrest becomes unoccupied.

3. The alarm system of claim 1 wherein said footrest is adapted to accommodate two feet of a user, said footrest supporting a pair of sensor pedals side by side and a sensor switch for each of said sensor pedals, each sensor connected in parallel to said electric circuit for creating an alarm in the event either sensor pedal is released.

4. The alarm system of claim 2, in which said electric circuit is incorporated into one or more housings mounted on one or both arm rests.

5. The alarm system of claim 4 in which said electric circuit incorporates one or both of two sound emitters or two flashing LED's, one of each being for each footrest.

6. The alarm system of claim 5 having a pair of housings, one of said housings mounted on one arm rest and the other of said housings mounted on a second arm rest, each housing containing a portion of said electric circuit including a sound emitter for each of said footrests for sounding an alarm when a footrest becomes unoccupied, and one of said housings containing a replaceable battery for said electric circuit.

7. The alarm system of claim 6 in which each housing additionally has a flashing LED for producing a light signal when a footrest becomes unoccupied.

8. A method of alarming a wheelchair comprising the steps of:

providing said wheelchair with a seat, arm rests, a back rest, and a footrest to support a foot of a user;

mounting a sensor pedal on said footrest of said wheelchair, said sensor pedal extending along one edge thereof from a spring hinge attached to said footrest, said spring hinge biasing a distal end of said sensor pedal away from said footrest;

bonding an actuating magnet to an underside of said distal end of said sensor pedal;

mounting a normally closed sensor switch on said footrest opposite said magnet whereas there is a gap between said magnet and said sensor switch when said footrest is unoccupied;

incorporating said sensor switch into an electric circuit which issues an alarm when said user's foot leaves said footrest at a time when said wheelchair is being occupied by said user;

the user's foot closing said gap when said foot is on said footrest, said magnet being in close proximity to said sensor switch causing said sensor switch to remain in an open position wherein said electric circuit is open and inactive;

the user's foot being removed from said footrest causing said gap to open and said magnet to move away from close proximity to said sensor causing said sensor switch to close said electric circuit resulting in an alarm being issued; and mounting an on-off switch in said seat for turning on said electric circuit when said wheelchair is occupied.

9. The method of claim 8 in which said wheelchair has two footrests, each footrest having a sensor pedal and a sensor connected in parallel to said electric circuit for creating an alarm in the event either footrest becomes unoccupied.

10. The method of claim 8 wherein said footrest accommodates both feet of a user, said footrest supporting a pair of sensor pedals side by side and a sensor switch for each of said sensor pedals, each sensor connected in parallel to said electric circuit for creating an alarm in the event either sensor pedal is released.

11. The method of claim 9, including the step of incorporating said electric circuit in one or more housings mounted on one or both arm rests.

12. The method of claim 9 including the step of incorporating one or both of two sound emitters or two flashing LED's, one of each being for each footrest into said housings.

13. The method of claim 9 including the step of providing a pair of housings, one of said housings mounted on one arm rest and the other of said housings mounted on a second arm rest, each housing containing a portion of said electric circuit including a sound emitter for each of said footrests for sounding an alarm when a footrest becomes unoccupied, and one of said housings containing a replaceable battery for said electric circuit.

14. The method of claim 13 in which each housing additionally has a flashing LED for producing a light signal when a footrest becomes unoccupied.

15. An alarm system for a wheelchair comprising:

said wheelchair comprising a seat, arm rests, a back rest, and a footrest adapted to support a foot of a user;

a sensor pedal mounted on said footrest, said sensor pedal extending along one edge thereof from a flexible joint attached to said footrest, said flexible joint biasing a distal end of said sensor pedal away from said footrest;

an actuator bonded to an underside of said distal end of said sensor pedal;

a normally closed sensor switch mounted on said footrest opposite said actuator whereas there is a gap between said actuator and said sensor switch when said footrest is unoccupied;

said sensor switch being part of an electric circuit which issues an alarm when said footrest becomes unoccupied when said wheelchair is being occupied;

said gap being closed when said footrest is being occupied, said actuator being in close proximity to said sensor switch to maintain said sensor switch in an open position wherein said electric circuit is open and inactive, said gap upon being opened when said footrest becomes unoccupied causing said sensor switch to close said electric circuit resulting in an alarm being issued; and an on-off switch mounted in said seat for turning on said electric circuit when said wheelchair is occupied.

16. The alarm system of claim 15 in which said wheelchair has two footrests, each footrest having a sensor pedal and a sensor connected in parallel to said electric circuit for creating an alarm in the event either footrest becomes unoccupied.

17. The alarm system of claim 15 wherein said footrest is adapted to accommodate two feet of a user, said footrest supporting a pair of sensor pedals side by side and a sensor switch for each of said sensor pedals, each sensor connected in parallel to said electric circuit for creating an alarm in the event either sensor pedal is released.

18. The alarm system of claim 16, in which said electric circuit is incorporated into one or more housings mounted on one or both arm rests.

19. The alarm system of claim 18 in which said electric circuit incorporates one or both of two sound emitters or two flashing LED's, one of each being for each footrest.

20. The alarm system of claim 19 having a pair of housings, one of said housings mounted on one arm rest and the other of said housings mounted on a second arm rest, each housing containing a portion of said electric circuit including a sound emitter for each of said footrests for sounding an alarm when a footrest becomes unoccupied, and one of said housings containing a replaceable battery for said electric circuit.

21. The alarm system of claim 20 in which each housing additionally has a flashing LED for producing a light signal when a footrest becomes unoccupied.

* * * * *